United States Patent
Arakita et al.

(10) Patent No.: US 8,731,252 B2
(45) Date of Patent: May 20, 2014

(54) IMAGE PROCESSING APPARATUS AND IMAGE PROCESSING METHOD

(75) Inventors: Kazumasa Arakita, Nasushiobara (JP); Naoko Toyoshima, Yokohama (JP); Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1215 days.

(21) Appl. No.: 12/405,698

(22) Filed: Mar. 17, 2009

(65) Prior Publication Data

US 2009/0238424 A1    Sep. 24, 2009

(30) Foreign Application Priority Data

Mar. 19, 2008    (JP) .................. 2008-071800

(51) Int. Cl.
*A61B 5/05* (2006.01)

(52) U.S. Cl.
USPC ........................................ 382/128

(58) Field of Classification Search
USPC ........................................ 382/128
See application file for complete search history.

(56) References Cited

U.S. PATENT DOCUMENTS

| | | | | |
|---|---|---|---|---|
| 5,701,897 A | * | 12/1997 | Sano ............................. | 600/453 |
| 2003/0053667 A1 | | 3/2003 | Paragios et al. | |
| 2003/0097076 A1 | * | 5/2003 | Nambu et al. ................. | 600/504 |

FOREIGN PATENT DOCUMENTS

| | | |
|---|---|---|
| JP | 4-52872 A | 2/1992 |
| JP | 2002-306483 A | 10/2002 |
| JP | 2003-515404 A | 5/2003 |
| JP | 2003-190148 A | 7/2003 |
| JP | 2004-141245 A | 5/2004 |
| JP | 2005-270478 A | 10/2005 |
| JP | 3902765 | 1/2007 |
| JP | 2009-541777 A | 11/2009 |
| WO | WO 2005/058165 A1 | 6/2005 |
| WO | WO 2006/126020 A2 | 11/2006 |
| WO | WO 2008/002797 A2 | 1/2008 |

OTHER PUBLICATIONS

Japanese Office Action issued Sep. 18, 2012 in Patent Application No. 2008-071800 with English Translation.
Office Action issued Jun. 11, 2013, in Japanese Patent Application No. 2008-071800 with English translation.

* cited by examiner

*Primary Examiner* — Howard Weiss
*Assistant Examiner* — Tifney Skyles
(74) *Attorney, Agent, or Firm* — Oblon, Spivak, McClelland, Maier & Neustadt, L.L.P.

(57) ABSTRACT

A storage unit stores data of a first image associated with a contrast-enhanced cardiac region. A specification unit specifies a specific region included in the cardiac region on the basis of a distribution of pixel values of the data of the first image. A setting unit contracts the specified specific region, and set an ROI to the contracted specific region. A calculation unit calculates an index concerning the set ROI. The index is associated with a function of the specific region.

8 Claims, 4 Drawing Sheets

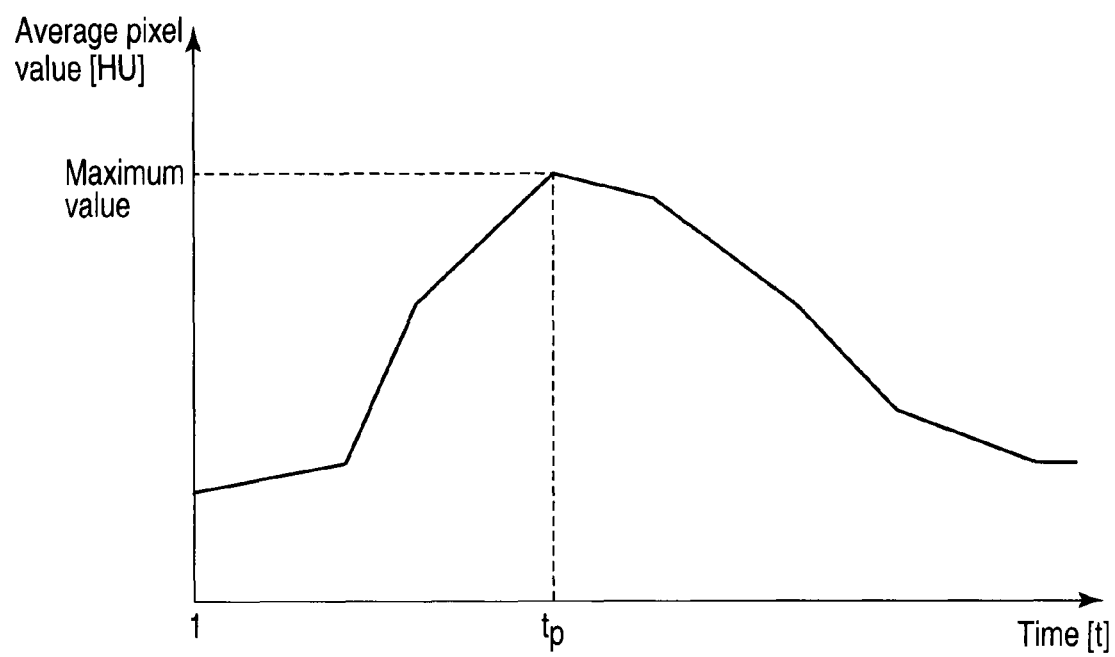
F I G. 3
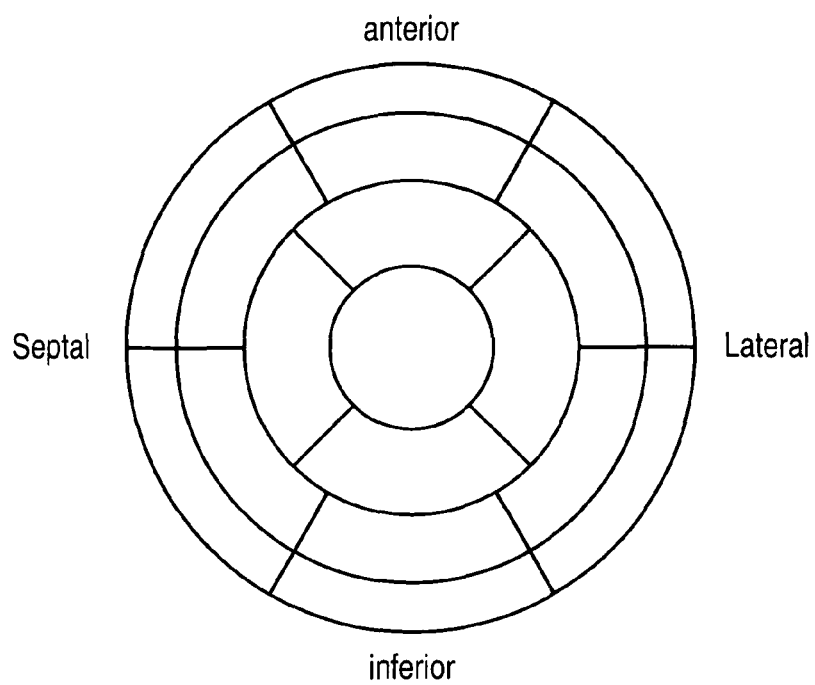
F I G. 5

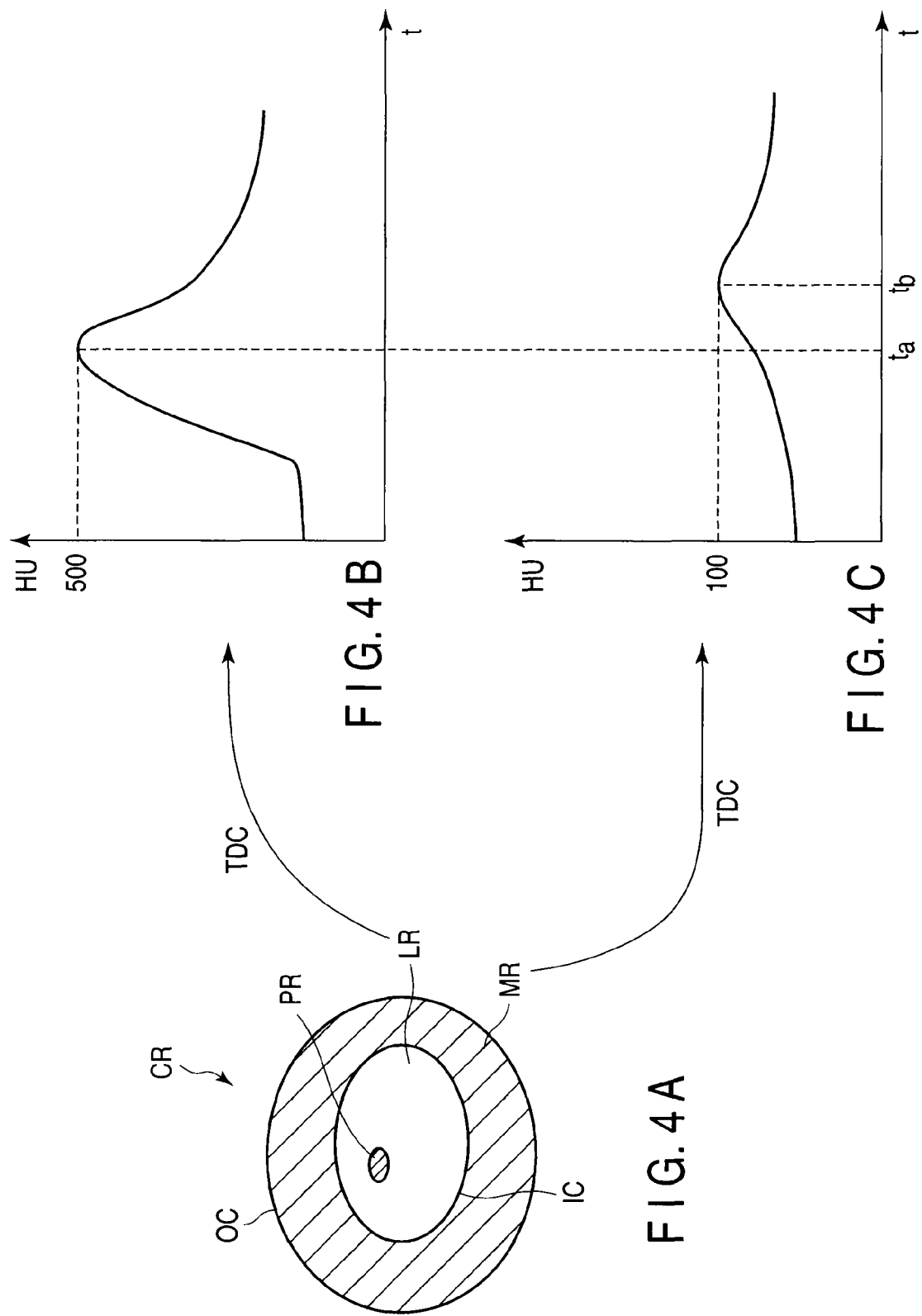

IMAGE PROCESSING APPARATUS AND IMAGE PROCESSING METHOD

CROSS-REFERENCE TO RELATED APPLICATIONS

This application is based upon and claims the benefit of priority from prior Japanese Patent Application No. 2008-071800, filed Mar. 19, 2008, the entire contents of which are incorporated herein by reference.

BACKGROUND OF THE INVENTION

1. Field of the Invention

The present invention relates to an image processing apparatus and image processing method which calculate indexes associated with the cardiac function of an subject to be examined, more specifically, indexes associated with the blood flow function.

2. Description of the Related Art

In X-ray CT examination, cardiac function analysis is performed. More specifically, blood flow analysis is performed on a left ventricular myocardial region. In blood flow analysis, an ROI (region of interest) (typically a left ventricular myocardial region) as an analysis target is set, and the change amount of contrast medium concentration in the set ROI is calculated. Various indexes associated with hemodynamics are then calculated on the basis of the calculated value. A typical blood flow analysis technique requires the data of the change amount of contrast medium concentration at a plurality of times.

As a technique of setting a myocardial region, the level set method disclosed in, for example, Japanese Patent No. 3902765 is known. According to such a conventional technique, any myocardial region cannot be specified in volume data at a time when no contrast medium is present, because the cardiac muscle is equal in pixel value to the lumen. In volume data with sufficient contrast based on a contrast medium, the contour of the myocardial region is faithfully specified, and an ROI is set to the specified myocardial region. For this reason, owing to the pulsation of the heart or a partial volume effect, the pixel values in the myocardial region are influenced by a contrast medium in a region other than the myocardial region, e.g., the left ventricular lumen and the pixel values in the papillary muscle region, lung region, or the like, and hence the accuracy of blood flow analysis decreases. Furthermore, when a plurality of ROIs are to be set in time-series volume data, since each ROI is set by repeating similar processing for the volume data, the amount of computation becomes enormous.

BRIEF SUMMARY OF THE INVENTION

It is an object of the present invention to provide an image processing apparatus and image processing method which can improve the accuracy of cardiac function analysis.

An image processing apparatus according to a first aspect of the present invention comprises: a storage unit configured to store data of a first image including a contrast-enhanced cardiac region; a first specification unit configured to specify a specific region included in the cardiac region on the basis of a distribution of pixel values of the data of the first image; a setting unit configured to contract the specified specific region, and set an ROI to the contracted specific region; and a calculation unit configured to calculate an index concerning the set ROI, the index being associated with a function of the specific region.

An image processing apparatus according to a second aspect of the present invention comprises: a storage unit configured to store data of a first image including a contrast-enhanced cardiac region; a specification unit configured to specify a myocardial region included in the cardiac region on the basis of a distribution of pixel values of the data of the first image; a setting unit configured to set an ROI to a region generated by contracting a thickness between an inner contour and an outer contour of the specified myocardial region; a calculation unit configured to calculate an index concerning the set ROI, the index being associated with a function of the myocardial region; a creation unit configured to create a map of the calculated index values by plotting the index values on polar coordinates for each of a plurality of slices associated with the myocardial region, each point of the polar coordinates being defined by angles around a long axis of the myocardial region and distances from an apex of the myocardial region; and a display unit configured to display the created map.

An image processing apparatus according to a third aspect of the present invention comprises: a storage unit configured to store time-series volume data including a contrast-enhanced cardiac region; a first specification unit configured to specify volume data associated with a specific time from the time-series volume data on the basis of a time-density curve based on the time-series volume data; a second specification unit configured to specify a specific region included in the cardiac region on the basis of a distribution of pixel values of the cardiac region included in the specified volume data; and a calculation unit configured to calculate an index associated with a function of the specific region for the specified specific region.

An image processing method according to a forth aspect of the present invention comprises: specifying a specific region included in a contrast-enhanced cardiac region from first image data on the basis of pixel values, the first image data including the cardiac region; contracting the specified specific region; setting an ROI to the contracted specific region; and calculating an index concerning the set ROI, the index being associated with a function of the specific region.

An image processing method according to a fifth aspect of the present invention comprises: specifying a specific region included in a contrast-enhanced cardiac region from image data on the basis of pixel values, the image data including the cardiac region; contracting the myocardial region by contracting a thickness between an inner contour and an outer contour of the specified myocardial region; setting an ROI to the contracted myocardial region; calculating indexes associated with a function of the myocardial region concerning the set ROI; creating a map of the calculated index values by plotting the index values on polar coordinates, each point of the polar coordinate being defined by angles around a long axis of a left ventricle of the myocardial region and distances from an apex of the myocardial region for each of a plurality of slices associated with the myocardial region; and displaying the created map.

An image processing method according to a sixth aspect of the present invention comprises: creating a time-density curve based on time-series volume data including a contrast-enhanced cardiac region; specifying volume data associated with a specific time from the time-series volume data on the basis of the created time-density curve; specifying a specific region included in the cardiac region from the specified volume data on the basis of pixel values; and calculating an index associated with a function of the specific region concerning the specified specific region.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a graph showing an example of the TDC created in step S1 in FIG. 2;

FIG. 4A is a view for explaining the processing in steps S3 and S4 in FIG. 2, showing the schematic structure of a left ventricular region;

FIG. 4B is a graph showing a TDC in a lumen region in the left ventricular region in FIG. 4A;

FIG. 4C is a graph showing a TDC in a myocardial region in the left ventricular region in FIG. 4A; and FIG. 5 is a view showing an example of a map on which indexes calculated in step S6 in FIG. 2 are plotted.

DETAILED DESCRIPTION OF THE INVENTION

An image processing apparatus and image processing method according to an embodiment of the present invention will be described below with reference to the views of the accompanying drawing. A characteristic feature of this embodiment is that when blood flow analysis is performed on a region of interest (to be referred to as an ROI hereinafter) of the heart of a subject on the basis of a plurality of volume data concerning the heart, the accuracy of blood flow analysis is improved by setting an ROI which is little influenced by the pulsation of the heart, a partial volume effect, and the like. Preferably, an ROI is set on a myocardial region of the left ventricle for blood flow analysis of the heart. Because a left ventricle is a main organ for driving blood throughout the body. Checking the hemodynamics of a left ventricular myocardial region helps to specify an abnormality in the cardiac function. Assume that an ROI according to this embodiment is set on a left ventricular myocardial region.

Note that medical equipment which generates volume data according to this embodiment is not limited to a specific apparatus. The modality to be used can be any of the following: an X-ray computer tomography (CT) apparatus, a single-photon-emission computer tomography (SPECT) apparatus, a positron emission tomography (PET) apparatus, a magnetic resonance imaging (MRI) apparatus, an ultrasonic diagnostic apparatus, and the like. This embodiment will exemplify an X-ray CT apparatus as medical equipment.

Figure 1:
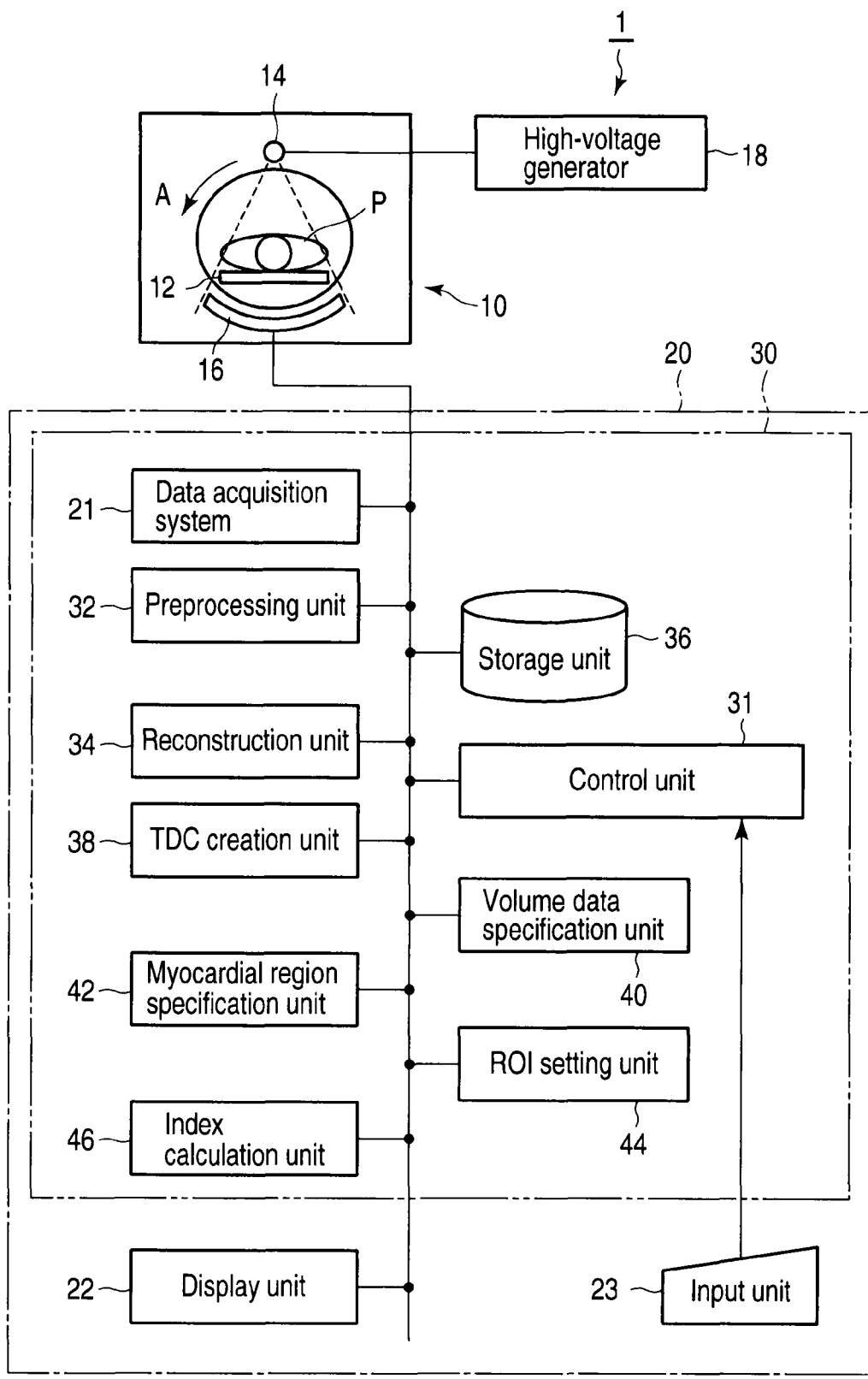
FIG. 1 is a block diagram showing the arrangement of an X-ray computer tomography apparatus according to an embodiment of the present invention.

FIG. 1 is a block diagram showing the arrangement of an X-ray CT apparatus 1 according to this embodiment. The X-ray CT apparatus 1 includes a scanning unit 10 and a computer apparatus 20. The scanning unit 10 rotatably supports an annular or disk-like rotating frame. The rotating frame has an X-ray tube 14 and an X-ray detector 16 which face each other through a subject P placed on a top 12 in a scan area. The rotating frame continuously rotates at high speed. The X-ray tube 14 generates X-rays upon receiving a high voltage and a filament current from a high-voltage generator 18. A data acquisition system (DAS) 21 is connected to the X-ray detector 16. The data acquisition system 21 acquires current signals from the respective channels of the X-ray detector 16. The X-ray detector 16 has a plurality of element arrays. Each of the arrays is arrayed along a slice direction (a direction along the rotation axis of the X-ray detector 16). Each of the arrays has a plurality of detection elements arrayed along the channel direction. The X-ray detector 16 has, for example, 256 or more element arrays.

The computer apparatus 20 includes an image processing apparatus 30, a display unit 22, and an input unit 23. The image processing apparatus 30 includes a control unit 31 functioning as a central unit, a preprocessing unit 32, a reconstruction unit 34, a storage unit 36, a TDC creation unit 38, a volume data specification unit 40, a myocardial region specification unit 42, an ROI setting unit 44, and an index calculation unit 46.

The preprocessing unit 32 performs logarithmic conversion processing for projection data from the data acquisition system 21, sensitivity correction for the X-ray detector 16, and the like. The reconstruction unit 34 generates time-series volume data $V_1, \ldots, V_n$ (n>1; n is an integer) at different scan times by repeating reconstruction processing for the projection data. The subscript 1 represents a time immediately after or before the injection of a contrast medium. The subscript n represents a time when the contrast medium flowing in the heart has become sufficiently diluted. Volume data includes a cardiac region. The volume data is constituted by a plurality of voxels which are three-dimensionally arranged. In the following description, voxels in volume data and pixels in image data will be generically called pixels without being discriminated.

The storage unit 36 stores projection data and time-series volume data $V_1$ to $V_n$. The storage unit 36 stores the volume data $V_1$ to $V_n$ in different files, respectively.

The TDC creation unit 38 creates a time-density curve (to be referred to as a TDC hereinafter) associated with the total time-series volume data $V_1$ to $V_n$ or a specific region.

The volume data specification unit 40 specifies a volume data $V_p$ (1<p≤n) from the time-series volume data $V_1$ to $V_n$ on the basis of the created TDC. For example, the specified volume data $V_p$ is relates to a time when the contrast medium has sufficiently flowed into the region. The specified volume data $V_p$ will be referred to as the reference volume data $V_p$ hereinafter.

The myocardial region specification unit 42 specifies a left ventricular myocardial region included in the reference volume data $V_p$ on the basis of the pixel value distribution of the reference volume data $V_p$. More specifically, the myocardial region specification unit 42 specifies a myocardial region by performing threshold processing for the reference volume data $V_p$ with a pixel value.

The ROI setting unit 44 contracts (thins) the specified myocardial region in the reference volume data $V_p$ toward the center of the myocardial region by performing erosion processing or the like, to generates a contracted region. And then The ROI setting unit 44 sets an ROI (to be referred to as a reference ROI hereinafter) to the contracted myocardial region for blood flow analysis. The ROI setting unit 44 deforms or moves the reference ROI in accordance with the shape or position of the left ventricular myocardial region included in another volume data $V_m$ (1<m≤n, m≠p) to set another ROI in another volume data $V_m$.

The index calculation unit 46 calculates various indexes associated with the function of a myocardial region, more specifically, various indexes associated with hemodynamics concerning the set ROI. The index calculation unit 46 calculates an index for each pixel constituting the ROI. The indexes include, for example, a blood flow rate in myocardial tissue per unit volume and unit time (BP [ml/100 ml/min]), blood flow rate in myocardial tissue per unit volume (BV [ml/100 ml]), and mean transit time (MTT [min]).

Figure 2:
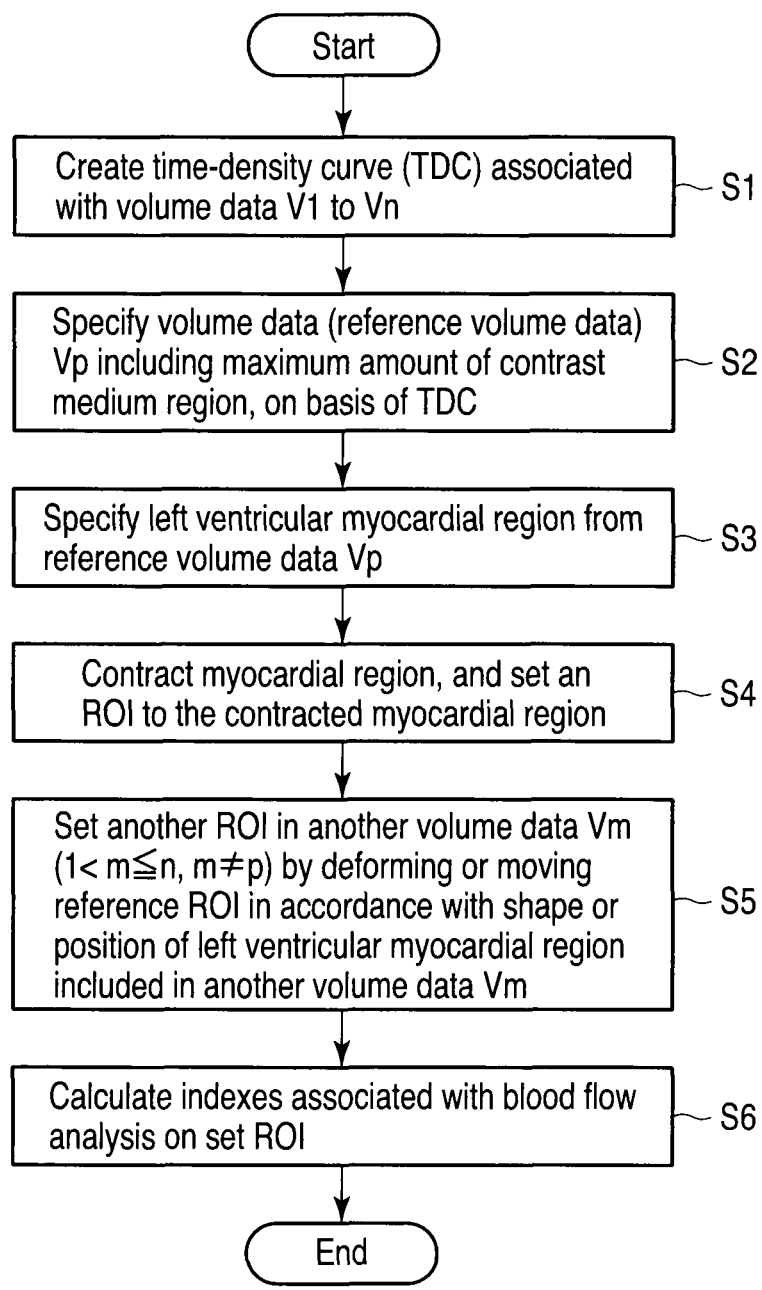
FIG. 2 is a flowchart showing the sequence of blood flow analysis processing by a control unit in FIG. 1.

Blood flow analysis processing by the control unit 31 will be described in detail below. FIG. 2 is a flowchart showing a sequence of blood flow analysis processing by the control unit 31. Assume that in this embodiment, a scan region is a chest portion including the heart of the subject. The X-ray CT apparatus 1 performs dynamic CT scan of the chest portion of the subject immediately after or before the injection of a contrast medium. Dynamic CT scan is to repeatedly perform CT scan for the same scan region. This dynamic CT scan generates the time-series volume data $V_1, V_2, \ldots, V_n$ corresponding to different scan times. More specifically, the reconstruction unit 34 performs ECG gated reconstruction processing for the projection data acquired by dynamic CT scan, to generate time-series volume data $V_1$ to $V_n$ concerning an end diastole. Limiting the volume data to be used to those at an end diastole can reduce motion artifacts due to pulsation, positional shifts between volume data, and the like. The storage unit 36 stores the generated volume data $V_1$ to $V_n$ in association with the scan times.

First of all, upon receiving a request to start blood flow analysis processing from the input unit 23 or the like, the control unit 31 causes the TDC creation unit 38 to perform TDC creation processing. In the TDC creation processing, the TDC creation unit 38 reads out the time-series volume data $V_1$ to $V_n$ from the storage unit 36 and creates a TDC concerning the time-series volume data $V_1$ to $V_n$ (step S1). More specifically, the TDC creation unit 38 calculates the average value of the pixel values of a plurality of pixels constituting each of a plurality of predetermined regions of the time-series volume data $V_1$ to $V_n$. The TDC creation unit 38 creates a TDC on the basis of the plurality of calculated average values. Note that a predetermined region can be the entire region of each volume data or a partial region of interest of each volume data (e.g., a left ventricular region or a left ventricular myocardial region).

FIG. 3 is a graph showing an example of a TDC to be created. As shown in FIG. 3, a TDC is a graph with the ordinate defining the average pixel value [HU] and the abscissa defining the scan time [t]. The TDC has a maximum value at a given time tp.

When a TDC is created, the control unit 31 causes the volume data specification unit 40 to perform volume data specification processing. In the volume data specification processing, the volume data specification unit 40 specifies the reference volume data $V_p$ from the time-series volume data $V_1$ to $V_n$ (step S2). More specifically, as shown in FIG. 3, the volume data specification unit 40 specifies the time tp when the average pixel value is maximum from the TDC, and specifies volume data (reference volume data $V_p$) associated with the specified time tp. Although the volume data corresponding to the maximum average pixel value is set as the reference volume data $V_p$, step S2 is not limited to this method. For example, volume data having an average pixel value equal to or more than a set threshold may be the reference volume data $V_p$. Alternatively, for example, the reference volume data $V_p$ can be specified by using the ratio between the number of maximum pixel values and the number of minimum pixel values, the standard deviation between pixel values, or a differential intensity.

When the reference volume data $V_p$ is specified, the control unit 31 causes the myocardial region specification unit 42 to perform myocardial region specification processing. The myocardial region specification unit 42 specifies a left ventricular myocardial region on the basis of the pixel value distribution of the reference volume data $V_p$ (step S3). Step S3 will be described in detail below. Assume that the center of volume data almost coincides with the anatomical center of the left ventricular region. A method of making them coincide with each other may be a method of making the center of a reconstruction region coincide with the left ventricular center at the time of scanning or a method of making the centers coincide with each other on volume data coordinates by image processing after the generation of volume data.

FIG. 4A is a view showing the schematic structure of a left ventricular region CR. FIG. 4A is a view schematically showing an axial slice of the left ventricular region CR. As shown in FIG. 4A, the left ventricular region CR includes a lumen region LR which is a blood flow channel. The left ventricular region CR has, outside the lumen region LR, a myocardial region MR for delivering blood to the aorta. Although not shown, capillary regions are vertically and horizontally distributed in the myocardial region MR. An inner contour IC (inner wall) of the myocardial region MR has countless fine folds. The left ventricular region CR also includes a papillary muscle region PR in the lumen region LR depending on a slice position. The papillary muscle region PR is connected to the myocardial region MR. The papillary muscle region PR protrudes from the myocardial region MR in the form of a cone. The papillary muscle region PR is not a target for blood flow analysis, and hence should not be included in an ROI.

FIG. 4B is a graph showing the TDC of the lumen region LR. FIG. 4C is a graph showing the TDC of the myocardial region MR. A contrast medium flows into the ventricular lumen and then flows into the cardiac muscle. As shown in FIGS. 4B and 4C, the lumen region LR reacts to the contrast medium earlier than the myocardial region MR, and undergoes less change in pixel value due to the contrast medium. In the reference volume data $V_p$, therefore, the pixel value difference between the myocardial region MR and the lumen region LR is large enough to discriminate the myocardial region MR from the lumen region LR by threshold processing.

The myocardial region specification unit 42 specifies the myocardial region MR by using the differences between the response characteristics of the respective tissues of the left ventricle concerning such a contrast medium, i.e., the pixel value differences between the myocardial region MR and the lumen region LR in the reference volume data $V_p$. The following is a specific sequence of this processing. First of all, the myocardial region specification unit 42 segments the volume data $V_p$ into a muscle region, a contrast medium region, and an air region by threshold processing (K-Means method). The myocardial region specification unit 42 then removes the papillary muscle region PR from the reference volume data $V_p$ on the basis of the characteristic shape or the like which the papillary muscle region PR has. This removal processing of the papillary muscle region PR is performed by an existing technique. When the papillary muscle region PR is removed, the myocardial region specification unit 42 specifies an outer contour OC of the myocardial region MR by searching the pixels in the preset myocardial region MR from an end portion of the reference volume data $V_p$ toward the center. The myocardial region specification unit 42 then specifies the inner contour IC of the myocardial region MR by searching the pixels in the myocardial region MR from the center of the reference volume data $V_p$ toward an end portion. The myocardial region specification unit 42 specifies, as the myocardial region MR, the region defined by the specified outer contour OC and the specified inner contour IC (the region between the outer contour OC and the inner contour IC).

Note that as another method of specifying a myocardial region, it suffices to use the level set method disclosed in Japanese Patent No. 3902765.

When a myocardial region is specified, the control unit 31 causes the ROI setting unit 44 to perform ROI setting processing. In the ROI setting processing, the ROI setting unit 44 contracts the myocardial region in accordance with the shape of the myocardial region, and sets a reference ROI to the contracted region (step S4). As concrete examples of contraction methods, various methods are conceivable. For example, the following method is available. First of all, the outer contour and inner contour of a myocardial region are respectively approximated to polyhedrons. The inner contour approximated to a polyhedron is enlarged toward the center of the myocardial region, and the outer contour approximated to a polyhedron is reduced toward the center of the myocardial region, thereby contracting the myocardial region. The inner contour approximated to the polyhedron is preferably enlarged until the ROI does not include any regions having folds, motion artifacts, and partial volume effects which are distributed in the inner contour of the myocardial region. Preset values can be used as a specific reduction width and enlargement width. Alternatively, a reduction width and an enlargement width may be determined on the basis of the heart rate of the subject, scanning conditions, and reconstruction conditions.

As another contraction method, there is available a method of contracting a myocardial region by erosion processing, i.e., replacing pixel values in an outer contour portion or inner contour portion of the myocardial region with, for example, pixel values in an air region so as to cut an outer contour portion or inner contour portion of the myocardial region.

When a reference ROI is set, the control unit 31 causes the ROI setting unit 44 to perform another ROI setting processing. In the another ROI setting processing, the ROI setting unit 44 sets another ROI in another volume data $V_m$ by deforming or moving a reference $ROI_p$ in accordance with the shape or position of the left ventricular myocardial region included in the another volume data $V_m$ (step S5). More specifically, the ROI setting unit 44 calculates the amount of positional shift between the center of the left ventricular region in the reference volume data $V_p$ and the center of the left ventricular region in another volume data $V_m$. The ROI setting unit 44 then moves the reference ROI in another volume data $V_m$ by the calculated amount of positional shift and sets the moved reference ROI as another ROI. Upon determining on the basis of pixel values that another ROI includes a region other than the myocardial region, the ROI setting unit 44 reduces another ROI until it does not include any region other than the myocardial region.

When an ROI is set, the control unit 31 causes the index calculation unit 46 to perform index calculation processing. In the index calculation processing, the index calculation unit 46 calculates indexes associated with hemodynamics of the ROI set in step S4 or S5 (step S6). Some indexes are calculated on the basis of a single ROI, and other indexes are calculated on the basis of a plurality of ROIs. The index calculation unit 46 plots the calculated indexes on a map like that shown in FIG. 5 in accordance with the types of indexes. An index map (polar map) is created by plotting indexes on a map. In this manner, the index calculation unit 46 also serves as an index map creation unit. A method of creating an index map is a known technique. Note that an index map is a map obtained by plotting indexes on polar coordinate. Each point on the polar coordinate is defined by angles around the long axis of the left ventricle and distances from the apex of the left ventricle. The plotted indexes are associated with a cardiac region. The plotted indexes are respectively calculated for a plurality of slices crossing the axis of the heart. More specifically, the center point of the circular map shown in FIG. 5 corresponds to the left ventricle apex. The distance (radius) from the center of the map represents the distance from the apex of the left ventricle to the basal along the long axis of the left ventricle. An azimuth of the map represents an angle around the long axis of the left ventricle. An index map can be created from another volume data $V_m$ in the same manner. A doctor or the like evaluates the cardiac function (e.g., the presence/absence of ischemia) of the subject by observing the index map displayed on the display unit 22.

Using ROI setting processing unique to this embodiment can improve the accuracy of blood flow analysis on a left ventricular myocardial region. This will be described in detail below by referring to myocardial perfusion analysis which is one of applications of blood flow analysis on a left ventricular myocardial region.

Myocardial perfusion analysis is performed by calculating indexes associated with the hemodynamics of a myocardial region and mapping the calculated indexes on a map. As described above, indexes are calculated on the basis of the CT value of a myocardial region. The most important item in myocardial perfusion analysis is the determination of a myocardial region (more specifically, the determination of the contour of a myocardial region) as an index calculation target region. The CT value of a myocardial region greatly differs from the CT value of a left ventricular lumen and the CT value of a lung region. As concrete numerical value examples, the CT values of a myocardial region, left ventricular lumen region, and lung region are 100 HU, 400 HU, and −900 HU, respectively. That is, if an index calculation processing target includes a region other than a myocardial region, e.g., a lumen region or a lung region, the values of the index map greatly deteriorate.

This embodiment has two steps, i.e., specifying a myocardial region and contracting the myocardial region, in order to accurately specify only a myocardial region. With these steps, a left ventricular lumen region or lung region which is the main factor that decreases the accuracy of myocardial perfusion analysis is removed from a myocardial perfusion analysis target (i.e., an index calculation target region).

Note that even if a myocardial region is contracted, the accuracy of myocardial perfusion analysis does not decrease. This is because an index for one pixel on a polar map is calculated on the basis of the CT values of plurality of pixels constituting a line segment (a set of pixels having the same angle around the long axis of the heart) set on a slice (the axial slice in FIG. 4) crossing the axis of the heart.

According to the above arrangement, the X-ray CT apparatus 1 sets an ROI to a contracted myocardial region (e.g., a region which does not include a left ventricular lumen region or a lung region) in blood flow analysis on the myocardial region, thereby removing a boundary portion of the myocardial region (a portion including at least an inner contour and an outer contour) which is a factor that decreases the accuracy of blood flow analysis from the ROI. As compared with the prior art in which blood flow analysis is performed on a region including a boundary portion of a myocardial region, therefore, the accuracy of blood flow analysis according to this embodiment improves. In addition, the X-ray CT apparatus 1 can automatically set another ROI in another volume data by simple image processing with a small processing amount by using a reference ROI set in reference volume data.

According to this embodiment, therefore, the accuracy of cardiac function analysis can be improved.

Note that the above blood flow analysis processing is performed for volume data constituted by a plurality of voxels. However, this blood flow analysis processing can be performed for volume data constituted by the data of many (e.g., 100) tomograms data (multi-slice image data) concerning an axial slice. In this case, blood flow analysis processing is performed for each of the tomograms constituting each of all volume data. That is, the ROI setting unit 44 sets an ROI in a left ventricular myocardial region for each tomogram in step S4, and the index calculation unit 46 calculates an index in step S6. Note that when multi-slice image data is to be processed, the inner and outer contours of the myocardial region in step S4 are approximated by polyhedrons. If the data of a plurality of images at different scan times are stored in the storage unit 36, it suffices to provide a specification unit which specifies reference image data on the basis of a time-density curve from a plurality of image data at different scan times in step S2.

In the above embodiment, the image processing apparatus 30 is included in the X-ray CT apparatus 1. However, the present invention is not limited to this. The image processing apparatus 30 can be a workstation connected to the X-ray CT apparatus 1 via an electric communication line.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
a first memory configured to store data of a first image including a contrast enhanced cardiac region;
a first specification unit configured to specify a specific region included in the cardiac region on the basis of a distribution of pixel values of the data of the first image;
a setting unit configured to contract the specified specific region, and set an ROI to the contracted specific region; and
a calculation unit configured to calculate an index concerning the set ROI, the index being associated with a function of the specific region,
wherein the first specification unit is configured to specify an outer contour and an inner contour of a myocardial region included in the cardiac region, and to specify, as the specific region, a region between the specified outer contour and the specified inner contour.

2. The apparatus according to claim 1, wherein the setting unit is configured to contract a thickness between the outer contour and the inner contour to generate the specific region, and set the ROI to the specific region.

3. The apparatus according to claim 1, wherein the first memory is configured to store data of a second image associated with the cardiac region and a scan time different from a scan time of the data of the first image, and
the setting unit is configured to move or deform the ROI in accordance with a position or shape of a myocardial region included in the second image, and set an ROI of a second image to the moved or deformed ROI.

4. The apparatus according to claim 1, further comprising:
a second memory configured to store data of time series images including the cardiac region, and
a second specification unit configured to specify the data of the first image associated with a first time from the data of the time series images on the basis of a time-density curve based on the data of the time series images.

5. The apparatus according to claim 1, wherein the calculation unit is configured to create a map of the calculated index values by plotting the index values on polar coordinates for each of a plurality of slices associated with the myocardial region, each point of the polar coordinates being defined by angles around a long axis of the myocardial region and distances from an apex of the myocardial region.

6. The apparatus according to claim 5, further comprising a display configured to display the created map.

7. An image processing apparatus, comprising:
a memory configured to store data of a first image including a contrast enhanced cardiac region;
a specification unit configured to specify a myocardial region included in the cardiac region on the basis of a distribution of pixel values of the data of the first image;
a setting unit configured to set an ROI to a region generated by contracting a thickness between an inner contour and an outer contour of the specified myocardial region;
a calculation unit configured to calculate an index concerning the set ROI, the index being associated with a function of the myocardial region;
a creation unit configured to create a map of the calculated index values by plotting the index values on polar coordinates for each of a plurality of slices associated with the myocardial region, each point of the polar coordinates being defined by angles around a long axis of the myocardial region and distances from an apex of the myocardial region; and
a display configured to display the created map.

8. An image processing apparatus, comprising:
a memory configured to store time series volume data including a contrast enhanced cardiac region;
a first specification unit configured to specify volume data associated with a specific time from the time series volume data on the basis of a time-density curve based on the time series volume data;
a second specification unit configured to specify a specific region included in the cardiac region on the basis of a distribution of pixel values of the cardiac region included in the specified volume data; and
a calculation unit configured to calculate an index associated with a function of the specific region for the specified specific region.

* * * * *